United States Patent [19]

Winternitz

[11] 4,255,436
[45] Mar. 10, 1981

[54] 2-OXO-3 THIAZOLINE-OXIMES AS PESTICIDES

[75] Inventor: Paul Winternitz, Greifensee, Switzerland

[73] Assignee: Hoffmann-La Roche Inc., Nutley, N.J.

[21] Appl. No.: 89,793

[22] Filed: Oct. 31, 1979

[30] Foreign Application Priority Data

Nov. 9, 1978 [CH] Switzerland ............... 11531/78
Aug. 24, 1979 [CH] Switzerland ............... 7728/79

[51] Int. Cl.³ ................... A01N 43/78; C07D 277/04
[52] U.S. Cl. ................................ 424/270; 548/191
[58] Field of Search ...................... 548/191; 424/270

[56] References Cited

U.S. PATENT DOCUMENTS 3,966,953  6/1976  D'Silva ........................... 424/270
4,181,661  1/1980  Rooney et al. ................... 424/270

*Primary Examiner*—Anton H. Sutto
*Attorney, Agent, or Firm*—Jon S. Saxe; George M. Gould; William H. Epstein

[57] ABSTRACT

Carbamoyl-oximes of the formula

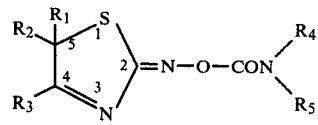

wherein $R_1$ and $R_3$ each are lower alkyl, lower alkenyl, cycloalkyl, aryl or halogen-substituted aryl; $R_2$ is lower alkyl; $R_4$ is lower alkyl or cycloalkyl; and $R_5$ is hydrogen, lower alkyl, lower alkylcarbonyl or halogen-substituted lower alkylcarbonyl, and acid addition salts of these compounds, a process for their preparation, pesticidal compositions containing one or more of these compounds as the active ingredient and methods for the use of such compositions for the control of pests.

33 Claims, No Drawings

2-OXO-3 THIAZOLINE-OXIMES AS PESTICIDES

DETAILED DESCRIPTION OF THE INVENTION

This invention is directed to carbamoyl-oximes of the formula

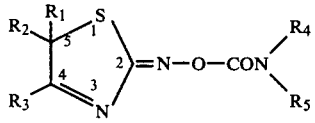
    I wherein $R_1$ and $R_3$ each are lower alkyl, lower alkenyl, cycloalkyl, aryl or halogen-substituted aryl; $R_2$ is lower alkyl; $R_4$ is lower alkyl or cycloalkyl; and $R_5$ is hydrogen, lower alkyl, lower alkylcarbonyl or halogen-substituted lower alkylcarbonyl, and acid addition salts of these compounds.

The compounds of formula I and their salts are useful for the control of pests and are especially suitable for the control of insects.

Accordingly, the invention is also directed to pesticidal compositions which contain one or more compounds of formula I or salts thereof as the active ingredient.

This invention is directed to processes for the preparation of these pesticidal compositions as well as methods for their use.

Finally, this invention is also directed to processes for the preparation of these compounds of formula I and their salts.

The compounds of this invention are prepared by the processes described below.

PROCEDURE A

An oxime of the general formula

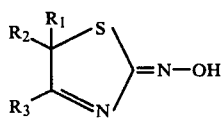
    II wherein $R_1$, $R_2$ and $R_3$ have the same significance as given earlier is reacted with an isocyanate of the general formula $$R_4-N=C=O \qquad \text{III}$$

wherein $R_4$ has the same significance as given above in the presence of a diluent and, optionally, in the presence of a catalyst. If desired, the resulting compound of formula I is converted with an acid into an acid addition salt.

In the oxime starting materials, as defined by formula II, $R_1$, $R_2$ and $R_3$ each preferably are a straight-chain or branched-chain alkyl containing from 1 to 3 carbons.

The oximes of formula II are novel. They are prepared by reacting an α-thiocyanato ketone of the formula

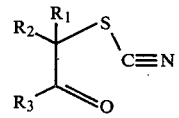
    V wherein $R_1$, $R_2$ and $R_3$ have the same significance as given above with hydroxylamine in the presence of a solvent, preferably an alcohol or an aqueous alcohol, at temperatures between 5° C. and 100° C., preferably between 25° C. and 40° C. The hydoxylamine is preferably used as a salt, especially as the hydrochloride. The reaction is carried out in the presence of an acid-binding agent such as sodium hydrogen carbonate or sodium acetate.

After the reaction is completed, the solvent is distilled off and the solid residue is digested with water, filtered off and dried. If desired, it may be recrystallized. Optionally, the product is dissolved in a suitable solvent, washed with water, dried over sodium sulfate and, after the solvent is distilled off, either recrystallized or purified chromatographically.

The α-thiocyanato ketones of formula V are generally known and can be prepared by such procedures as, for example, replacing the halogen atom of an α-halo ketone with the thiocyanato group using a metal rhodanide in a solvent such as acetone or dimethylformamide. The α-halo ketones are generally known and can be prepared by such procedures as, for example, halogenating carbonyl compounds with bromine in dioxane or with N-bromosuccinimide in carbon tetrachloride.

In the isocyanates of formula III, $R_4$ is, preferably, an alkyl group of from 1 to 3 carbons. These isocyanates are generally known compounds which can be prepared by, for example, reacting amines with phosgene and subsequently heating.

Diluents for the reaction of Procedure A include all inert organic solvents. Preferred solvents are ethers such as 1,2-dimethoxyethane, tetrahydrofuran and dioxane; ketones such as diethyl ketone and, especially, acetone and methyl ethyl ketone; nitriles such as propionitrile and, especially, acetonitrile; formamides such as dimethylformamide; and halogenated hydrocarbons such as methylene chloride, carbon tetrachloride and chloroform.

Preferred catalysts are tertiary bases such as triethylamine, pyridine, 1,4-diazabicyclo[2,2,2]octane and tin-organic compounds such as dibutyltin diacetate.

The reaction temperature can vary over a wide range. In general, the reaction is carried out at a temperature between 0° C. and 100° C., and, preferably, at between 30° C. and 85° C. When a solvent is present, the reaction is conveniently carried out at the boiling point of the solvent.

The reaction is preferably carried out using an excess of the isocyanate of formula III. The compounds of formula I are isolated by distilling off the solvent and working up the residue by standard procedures.

PROCEDURE B

An oxime of the general formula

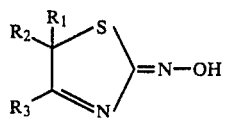

wherein $R_1$, $R_2$ and $R_3$ have the same significance as given above is reacted with a carbamoyl halide of the formula

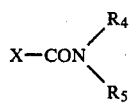

wherein $R_4$ and $R_5$ have the same significance as given above and X is halogen in the presence of a diluent and an acid-binding agent. If desired, the resulting compound of formula I is converted with an acid into an acid addition salt.

The oximes are prepared as described in Procedure A above.

In the carbamoyl halides of formula IV, $R_4$ is, preferably, an alkyl group of from 1 to 3 carbons and $R_5$ is, preferably, hydrogen or an alkyl of from 1 to 3 carbons and, especially, methyl. The carbamoyl halides are generally known compounds which can be prepared, for example, by reacting amines with phosgene.

Diluents for the reaction of Procedure B include all inert organic solvents. Preferred solvents are those mentioned for Procedure A above.

The reaction is carried out in the presence of an acid-binding agent. While any organic or inorganic acid-binding agent can be used, the preferred acid-binding agents are alkali carbonates such as sodium carbonate, potassium carbonate and sodium hydrogen carbonate; lower tertiary alkylamines, cycloalkylamines and arylalkylamines such as triethylamine and dimethylbenzylcyclohexylamine; pyridine and diazabicyclooctane.

The reaction temperature can vary over a wide range. In general, the reaction is carried out at a temperature between 0° C. and 100° C. and, preferably, between 0° C. and 40° C.

The reaction is preferably carried out using 1 to 2 mol of the carbamoyl halide for each mol of the oxime. A slight excess of the acid-binding agent (up to ca 30 wt. %) is advantageous. The isolation of the compounds of formula I is carried out using standard procedures.

The conversion of a compound of formula I into an acid addition salt by an acid is carried out using standard procedures.

The term "lower alkyl" used herein denotes both straight-chain and branched-chain hydrocarbon groups containing from 1 to 5 carbons such as methyl, ethyl, propyl, isopropyl and the like. This connotation also applies to those groups containing lower alkyl moieties such as lower alkylcarbonyl and halogen-substituted lower alkylcarbonyl. The term "lower alkenyl" denotes straight-chain and branched-chain unsaturated hydrocarbon groups containing from 2 to 5 carbon atoms such as vinyl, allyl, butenyl and pentenyl. The term "halogen" includes fluorine, chlorine, bromine and iodine unless expressly stated otherwise. The term "aryl" refers to aromatic hydrocarbons of which phenyl and naphthyl are preferred. The term "cycloalkyl" includes cyclic groups of from 3 to 6 carbons.

The acid addition salts of the compounds of formula I are physiologically compatible salts. Preferred salts are those formed with hydrohalic acids (e.g., hydrochloric acid and hydrobromic acid), phosphoric acid, nitric acid, mono- and bifunctional carboxylic acids and hydroxycarboxylic acids such as acetic acid, maleic acid, succinic acid, fumaric acid, tartaric acid, citric acid, salicylic acid, sorbic acid and lactic acid, and sulfonic acids such as 1,5-naphthalene-disulfonic acid. The acid addition salts are, compared to the bases of formula I, of less importance.

The invention also encompasses the syn- and anti-forms of the compounds of formula I.

Compounds of formula I in which $R_1$, $R_2$ and $R_3$ each are alkyl containing from 1 to 3 carbons are preferred. Also preferred are compounds of formula I in which $R_4$ is alkyl of from 1 to 3 carbons and $R_5$ is hydrogen.

Especially preferred compounds of formula I are:

2-oxo-4,5,5-trimethyl-3-thiazoline-O-(methylcarbamoyl)-oxime;

2-oxo-4,5-dimethyl-5-ethyl-3-thiazoline-O-(methylcarbamoyl)-oxime; and 2-oxo-4,5-diethyl-5-methyl-3-thiazoline-O-(methylcarbamoyl)-oxime.

The compounds of this invention are active as pesticides and, in particular, for the control of insects, mites and nematodes.

They are especially valuable against:

(a) Coleoptera such as Epilachna spp., *Leptinotarsa decemlineata*, Anthonomus spp., *Conotrachelus nenuphar*, Lema spp., *Lissorhoptrus cryzaephilus*, Phyllotreta spp., *Psylliodes chrysocephala*, *Meligethes aenus*, *Ceutorrhynchus assimilis*, Agriotes spp., *Melolontha melolontha*, Diabrotica spp.;

(b) Lepidoptera such as Laspeyresia spp., *Adoxophyes orana*, *Tortrix viridana*, *Cheimatobia brumata*, *Lyonetia clerkella*, *Operophtera brumata*, *Lithocolletis blancardella*, *Porthetria dispar*, *Mamestra brassicae*, *Agrotis segetum*, Plutella spp., *Pieris brassicae*, *Choristoneura fumiferana*, Heliothis spp., Spodoptera spp., *Pectinophora gossipiella*, Chilo spp., *Ostrinia nubilalis*, *Clysia ambiguella, Lobesia botrana;*

(c) Diptera such as *Drosophila melanogaster*, Ceratitis spp., *Oscinella frit*, Dacus spp., Rhagoletis spp., Leatherjacket spp.;

(d) Homoptera, i.e. aphids, such as *Aphis fabae, Myzus persicae* and further species of these genera, Rhophalosiphon spp., Schizaphis spp., Dysaphis spp., Eriosoma spp., Macrosiphum spp., Adelges spp., *Sitobion avenae, Metopolophium dirhodum* as well as shield and soft lice such as, for example, Aspidiotus spp., Saissetia spp., *Quadraspidiotus perniciosus, Aonidiella aurantii*, Coccus spp., Lepidosaphes spp., Planococcus spp., Pseudococcus spp., Ceroplastes spp., *Icerya purchasi*, Chrysomphalus spp., Parlatoria spp., as well as cicades such as Nephotettix spp., Laodelphax spp., Nilaparvata spp., Sogatella spp., Erythroneura spp.;

(e) Aleyrodidae such as *Trialeurodes vaporariorum*, Dialeurodes spp., Aleurothrixus spp., Bemisia spp., Aleyrodes spp., as well as thrips species and bugs;

(f) Acarina such as *Tetranychus urticae, Panonychus ulmi* and other Tetranychida, Tarsonemida such as Steneotarsonemus spp., Tenuipalpida such as Brevipalpus, Eriophyida such as *Phyllocoptruta oleivora, Aceria sheldoni*, Eriophyes spp., Aceria spp., as well as ticks; and (g) Nematoda such as free-living nematodes (inter alia Pratylenchus spp. such as *P. penetrans*), leaf-parasitic nematodes (inter alia Aphelenchoides), root-parasitic nematodes (inter alia Meloidogynae spp. such as *M. incognita*, Globodera spp. such as *G. rostochiensis*).

The instant invention is also directed to pesticidal compositions such as solutions, emulsions, suspensions, powders, pastes and granulates which contain inert carrier materials and, as the active ingredient, one or more of the compounds of formula I.

These compositions are prepared by known methods such as, for example, by mixing the active substance with extenders (liquid solvents, liquified gases under pressure and/or solid carrier substances) and, if desired, surface-active agents (emulsifiers or dispersing agents). When water is used as the extender, organic solvents can also be used as auxiliary solvents.

Examples of liquid solvents include: aromatics such as xylene, toluene, benzene and alkyl-naphthalenes; chlorinated aromatics and chlorinated aliphatic hydrocarbons such as chlorobenzene, chloroethylene and methylene chloride; aliphatic hydrocarbons such as cyclohexane and paraffins (e.g., petroleum fractions); alcohols such as butanol and glycol as well as their ethers and esters; ketones such as acetone, methyl ethyl ketone, methyl isobutyl ketone and cyclohexanone; strongly polar solvents such as dimethylformamide and dimethylsulfoxide and water.

Examples of liquified gaseous extenders or carrier substances include liquids which are gaseous at normal temperature and under normal pressure such as aerosol carrier gases such as halogenated hydrocarbons (e.g. Freon).

Examples of solid carrier substances include natural mineral powders such as kaolins, clays, talc, chalk, quartz, attapulgite, montmorillonite and diatomaceous earth, and synthetic mineral powders such as high-dispersible silicic acid, aluminum oxide and silicates.

Emulsifying agents suitable for use in the pesticidal compositions of this invention can be non-ionic or anionic. Examples of non-ionic emulsifiers which can be used include polyoxyethylene-fatty acid esters and polyoxyethylene-fatty alcohol ethers such as alkylarylpolyglycol ethers. Examples of anionic emulsifiers include alkyl sulfonates, alkyl sulfates and aryl sulfonates.

Examples of dispersing agents include lignin, sulfite lyes and methyl cellulose.

The active ingredients of this invention can be present in the composition in admixture with other known active substances. The compositions generally contain between 0.1 wt. % and 95 wt. % of total active substances, preferably between 0.5 wt. % and 40 wt. %.

The active ingredients can also be used as such in the compositions or in application forms prepared from these compositions such as ready-for-use solutions, emulsions, foams, suspensions, powders, pastes, soluble powders, dusting agents and granulates. They are used in the usual procedures such as squirting, spraying, smoke-screening, dusting, scattering, drilling-in, vaporizing, pouring, drenching or incrustating.

The concentrations of active ingredient in the ready-for-use preparations can vary over wide limits. In general, the concentration lies between 0.0001 wt. % and 10 wt. %, preferably between 0.01 wt. % and 1 wt. %.

The active ingredients can also be used with good effect in the ultra-low-volume process (ULV) where it is possible to produce compositions having up to 95% or even 100% of active ingredient alone.

The compounds of this invention exhibit good activity against plant-damaging insects, nematodes and mites.

The following examples illustrate the efficacy of the compounds of this invention against various pests including aphids, cicades and spider mites.

In these examples, "compound A" is the compound of the formula

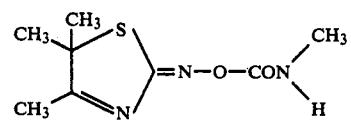

EXAMPLE 1

This example illustrates the activity of a compound of this invention against *Leptinotarsa decemlineata* (Colorado potato beetle).

Potato leaf roundels were sprayed with a solution of the active ingredient in acetone. Five freshly hatched larvae in the first stage were placed on each roundel, incubated at 25° C. and 60% relative humidity and, after 2 days, re-fed with two untreated roundels per batch. Untreated leaf roundels and leaf roundels treated with acetone were used as the controls. The test duration was 4 days. The results, listed in Table 1 below, are expressed as the percentage reduction in the survival rate of the larvae compared with controls.

TABLE 1

| Active Ingredient | Dosage ($10^{-x}$ g AI/cm$^2$) | % Activity |
|---|---|---|
| Compound A | x = 5 | 100 |
|  | 6 | 100 |
|  | 7 | 100 |
|  | 8 | 0 |

(Untreated controls: 5% mortality)
AI = active ingredient

EXAMPLE 2

This example illustrates the activity of Compound A as an ovicide against *Tetranychus urticae* (common spider mite).

Leaf roundels of bush beans were infected with 10 adult females. One day later the females were removed and the leaf roundels carrying 70 to 100 eggs were sprayed with a solution of the active ingredient in acetone. The treated roundels were placed on moist foam material and incubated at 25° C. and 60% relative humidity. Untreated leaf roundels and leaf roundels treated with acetone were used as the controls. The test duration was 6 days. The results, listed in Table 2 below, are expressed as the percentage reduction in the hatching rate of the eggs.

TABLE 2

| Active Ingredient | Dosage ($10^{-x}$ g AI/cm$^2$) | % Activity |
|---|---|---|
| Compound A | x = 5 | 100 |
|  | 6 | 100 |
|  | 7 | 44 |

(Untreated controls: 3% egg mortality)
AI = active ingredient

EXAMPLE 3

This example illustrates the activity of Compound A in a UV persistence test against *Musca domestica* (common house fly).

This test measures the efficacy of the active substance after 72 hours preincubation under UV and also by comparison with the efficacy of the active substance without pre-incubation under UV.

The bases of 9 cm. diameter Petri dishes were treated with a solution of the active substance in acetone and pre-incubated for 72 hours under UV light (Philips TOA 40 W/05) at 28° C. and 60% relative humidity. Ten female flies (4–5 days old) were then placed in each Petri dish and incubated at 25° C. and 60% relative humidity. Untreated Petri dishes and Petri dishes treated with acetone were used as the controls. The test duration was 72 hours under UV and 24 hours after the flies were placed in the dishes. The results, listed in Table 3 below, are expressed as the percentage reduction in the survival rate of the flies compared with the controls.

TABLE 3

| Active Ingredient | Dosage ($10^{-x}$ g AI/cm$^2$) | % Activity (after 72 hrs pre-incubation under UV) | % Activity (without pre-incubation) |
|---|---|---|---|
| Compound A | x = 5 | 100 | 100 |
| | 6 | 100 | 100 |
| | 7 | 0 | 95 |
| | 8 | | 2 |

(Untreated control lots: 0% mortality)
AI = active ingredient

The following examples illustrate the production of the compounds of formula I of this invention.

EXAMPLE 4

15.8 g (0.1 mol) of 2-oxo-4,5,5-trimethyl-3-thiazoline-oxime and 8.5 g. (0.15 mol) of methyl isocyanate were dissolved in 100 ml. of anhydrous dichloromethane. After a few drops of triethylamine were added to this solution, the mixture warmed to 40°–45° C. The mixture was warmed to 50°–60° C. for a short time and then the solvent was distilled off under vacuum. The residue was dissolved in 50 ml. of hot ethyl acetate, treated with carbon and filtered. The hot filtrate was concentrated to 20–30 ml. and treated with 20–30 ml. of hexane. The precipitated crystals were filtered off under vacuum, washed with ether and dried to yield 2-oxo-4,5,5-trimethyl-3-thiazoline-O-(methylcarbamoyl)-oxime, m.p. 123°–125° C.

EXAMPLE 5

15.8 g. (0.1 mol) of 2-oxo-4,5,5-trimethyl-3-thiazoline-oxime and 15.2 g. (0.15 mol) of triethylamine were dissolved in 100 ml. of anhydrous 1,2-dimethoxy-ethane. 16.1 g. (0.15 mol) of dimethylcarbamoyl chloride were added dropwise. The mixture was refluxed for 3 hours and the solvent was distilled off under vacuum. The residue was dissolved in 100 ml. of dichloromethane and washed with water. After the organic phase was dried over sodium sulfate, the solvent was distilled off. The residue was purified chromatographically on silica gel using ether/dichloromethane (9:1) for the elution to yield 2-oxo-4,5,5-trimethyl-3-thiazoline-O-(dimethylcarbamoyl)-oxime, m.p. 108°–110° C.

EXAMPLE 6

2-oxo-4-ethyl-5,5-dimethyl-3-thiazoline-oxime was reacted with methyl isocyanate as described in Example 4 to yield 2-oxo-4-ethyl-5,5-dimethyl-3-thiazoline-O-(methylcarbamoyl)-oxime, m.p. 98°–100° C. The 2-oxo-4-ethyl-5,5-dimethyl-3-thiazoline-oxime starting material (m.p. 178°–180° C.) was prepared from 2-methyl-2-thiocyanato-3-pentanone (b.p. [0.03 mm] 56°–58° C.).

EXAMPLE 7

2-oxo-4-isopropyl-5,5-dimethyl-3-thiazoline-oxime was reacted with methyl isocyanate as described in Example 4 to yield 2-oxo-4-isopropyl-5,5-dimethyl-3-thiazoline-O-(methylcarbamoyl)-oxime, m.p. 89°–91° C. The 2-oxo-4-isopropyl-5,5-dimethyl-3-thiazoline-oxime starting material (m.p. 220°–222° C.) was prepared from 2,4-dimethyl-2-thiocyanato-3-pentanone (b.p. [0.02 mm] 64°–66° C.).

EXAMPLE 8

2-oxo-4,5,5-trimethyl-3-thiazoline-oxime was reacted with ethyl isocyanate as described in Example 4 to yield 2-oxo-4,5,5-trimethyl-3-thiazoline-O-(ethylcarbamoyl)-oxime, m.p. 84°–86° C.

EXAMPLE 9

2-oxo-4-phenyl-5,5-dimethyl-3-thiazoline-oxime was reacted with methyl isocyanate as described in Example 4 to yield 2-oxo-4-phenyl-5,5-dimethyl-3-thiazoline-O-(methylcarbamoyl)-oxime, m.p. 135°–137° C. The 2-oxo-4-phenyl-5,5-dimethyl-3-thiazoline-oxime starting material (m.p. 147°–149° C.) was prepared from 2-methyl-1-phenyl-2-thiocyanato-1-propanone (b.p. [0.02 mm] 98°–100° C.).

EXAMPLE 10

2-oxo-4,5,5-trimethyl-3-thiazoline-oxime was reacted with isopropyl isocyanate as described in Example 4 to yield 2-oxo-4,5,5-trimethyl-3-thiazoline-O-(isopropylcarbamoyl)-oxime, m.p. 114°–116° C.

EXAMPLE 11

2-oxo-4,5,5-trimethyl-3-thiazoline-oxime was reacted with cyclopropyl isocyanate as described in Example 4 to yield 2-oxo-4,5,5-trimethyl-3-thiazoline-O-(cyclopropylcarbamoyl)-oxime, m.p. 86°–89° C.

EXAMPLE 12

2-oxo-4,5,5-trimethyl-3-thiazoline-oxime was reacted with cyclobutyl isocyanate as described in Example 4 to yield 2-oxo-4,5,5-trimethyl-3-thiazoline-O-(cyclobutylcarbamoyl)-oxime, m.p. 94°–96° C.

EXAMPLE 13

2-oxo-4-propyl-5,5-dimethyl-3-thiazoline-oxime was reacted with methyl isocyanate as described in Example 4 to yield 2-oxo-4-propyl-5,5-dimethyl-3-thiazoline-O-(methylcarbamoyl)-oxime, m.p. 112°–114° C. The 2-oxo-4-propyl-5,5-dimethyl-3-thiazoline-oxime starting material melts at 145°–147° C.

EXAMPLE 14

2-oxo-4-cyclohexyl-5,5-dimethyl-3-thiazoline-oxime was reacted with methyl isocyanate as described in Example 4 to yield 2-oxo-4-cyclohexyl-5,5-dimethyl-3-thiazoline-O-(methylcarbamoyl)-oxime, m.p. 158°–160°

C. The 2-oxo-4-cyclohexyl-5,5-dimethyl-3-thiazoline-oxime starting material melts at 159°–162° C.

EXAMPLE 15

2-oxo-4,5-dimethyl-5-ethyl-3-thiazoline-oxime was reacted with methyl isocyanate as described in Example 4 to yield 2-oxo-4,5-dimethyl-5-ethyl-3-thiazoline-O-(methylcarbamoyl)-oxime, m.p. 115°–117° C. The 2-oxo-4,5-dimethyl-5-ethyl-3-thiazoline-oxime starting material melts at 143.5°–144.5° C.

EXAMPLE 16

2-oxo-4,5-diethyl-5-methyl-3-thiazoline-oxime was reacted with methyl isocyanate as described in Example 4 to yield 2-oxo-4,5-diethyl-5-methyl-3-thiazoline-O-(methylcarbamoyl)-oxime, m.p. 88°–90° C. The 2-oxo-4,5-diethyl-5-methyl-3-thiazoline-oxime starting material melts at 125°–128° C.

EXAMPLE 17

2-oxo-4,5-dimethyl-5-propyl-3-thiazoline-oxime was reacted with methyl isocyanate as described in Example 4 to yield 2-oxo-4,5-dimethyl-5-propyl-3-thiazoline-O-(methylcarbamoyl)-oxime, m.p. 66°–69° C. The 2-oxo-4,5-dimethyl-5-propyl-3-thiazoline-oxime starting material melts at 94°–96° C.

EXAMPLE 18

2-oxo-4-propyl-5-ethyl-5-methyl-3-thiazoline-oxime was reacted with methyl isocyanate as described in Example 4 to yield 2-oxo-4-propyl-5-ethyl-5-methyl-3-thiazoline-O-(methylcarbamoyl)-oxime, m.p. 124°–126° C. The 2-oxo-4-propyl-5-ethyl-5-methyl-3-thiazoline-oxime starting material melts at 132°–135° C.

EXAMPLE 19

2-oxo-4-butyl-5,5-dimethyl-3-thiazoline-oxime was reacted with methyl isocyanate as described in Example 4 to yield 2-oxo-4-butyl-5,5-dimethyl-3-thiazoline-O-(methylcarbamoyl)-oxime, m.p. 128°–130° C. The 2-oxo-4-butyl-5,5-dimethyl-3-thiazoline-oxime starting material melts at 117°–119° C.

EXAMPLE 20

2-oxo-4,5-dimethyl-5-isobutyl-3-thiazoline-oxime was reacted with methyl isocyanate as described in Example 4 to yield 2-oxo-4,5-dimethyl-5-isobutyl-3-thiazoline-O-(methylcarbamoyl)-oxime, m.p. 99°–101° C. The 2-oxo-4,5-dimethyl-5-isobuty-3-thiazoline-oxime starting material melts at 105°–107° C.

EXAMPLE 21

2-oxo-4,5-dimethyl-5-pentyl-3-thiazoline-oxime was reacted with methyl isocyanate as described in Example 4 to yield 2-oxo-4,5-dimethyl-5-pentyl-3-thiazoline-O-(methylcarbamoyl)-oxime as a viscous oil; $n_D^{44.5}=1.5256$. The 2-oxo-4,5-dimethyl-5-pentyl-3-thiazoline-oxime starting material melts at 104°–106° C.

EXAMPLE 22

2-oxo-4-(p-chlorophenyl)-5,5-dimethyl-3-thiazoline-oxime was reacted with methyl isocyanate as described in Example 4 to yield 2-oxo-4-(p-chlorophenyl)-5,5-dimethyl-3-thiazoline-O-(methylcarbamoyl)-oxime, m.p. 147°–149° C. The 2-oxo-4-(p-chlorophenyl)-5,5-dimethyl-3-thiazoline-oxime starting material melts at 205°–207° C.

EXAMPLE 23

2-oxo-4,5-dimethyl-5-butyl-3-thiazoline-oxime was reacted with methyl isocyanate as described in Example 4 to yield 2-oxo-4,5-dimethyl-5-butyl-3-thiazoline-O-(methylcarbamoyl)-oxime as a viscous oil; $n_D^{44.5}=1.5324$. The 2-oxo-4,5-dimethyl-5-butyl-3-thiazoline-oxime starting material melts at 100°–102° C.

EXAMPLE 24

2-oxo-4,5-dimethyl-5-(3-methyl-2-pentenyl)-3-thiazoline-oxime was reacted with methylisocyanate as described in Example 4 to yield 2-oxo-4,5-dimethyl-5-(3-methyl-2-pentenyl)-3-thiazoline-O-(methylcarbamoyl)-oxime as a viscous oil; $n_D^{20}=1.5424$.

The 2-oxo-4,5-dimethyl-5-(3-methyl-2-pentenyl)-3-thiazoline-oxime used as the starting material was prepared as follows:

5 g. of 3,6-dimethyl-5-octen-2-one were treated dropwise with a solution of 18.5 g. of 2-carboxyethyl-triphenylphosphonium perbromide in 30 ml. of tetrahydrofuran. The mixture was stirred at room temperature overnight. The insoluble bromide was filtered off and the filtrate was poured into 5% aqueous sodium carbonate solution and extracted twice with ether. The extracts were washed with water and sodium chloride solution, dried over sodium sulfate and evaporated. The residue was distilled in a bulb-tube at 60° C./0.06 Torr. The resulting crude 3-bromo-3,6-dimethyl-5-octen-2-one was purified using potassium rhodanide to give 2-oxo-4,5-dimethyl-5-(3-methyl-2-pentenyl)-3-thiazoline-oxime; $n_D^{20}=1.5432$.

EXAMPLE 25

7.9 g. of 2-oxo-4,5,5-trimethyl-3-thiazoline-oxime were dissolved in 100 ml. of acetonitrile and 6.9 g. of potassium carbonate were added to the solution. The mixture was cooled to 0° C. and treated dropwise, with rapid stirring, with a solution of 6.8 g. of N-acetyl-N-methylcarbamoyl chloride in 25 ml. of acetonitrile. After the addition was completed, the ice-bath was removed and the mixture was stirred at room temperature for 2 hours.

The mixture was filtered and the filtrate was concentrated on a rotary evaporator. The residue was poured into semi-saturated sodium chloride solution and extracted three times with ethyl acetate. The extracts were washed with semisaturated sodium chloride solution and saturated sodium chloride solution, dried over sodium sulfate and evaporated. The product was crystallized from hexane/ethyl acetate to pure 2-oxo-4,5,5-trimethyl-3-thiazoline-O-[methyl(acetyl)carbamoyl]-oxime, m.p. 119°–124° C.

2-oxo-4,5-dimethyl-5-ethyl-3-thiazoline-oxime was reacted with N-acetyl-N-methyl-carbamoyl chloride as described above to yield 2-oxo-4,5-dimethyl-5-ethyl-3-thiazoline-O-[methyl(acetyl)carbamoyl]oxime, m.p. 98°–101° C.

EXAMPLE 26

2-oxo-4,5,5-trimethyl-3-thiazoline-oxime, the starting material in Examples 4, 5, 8, 10–12 and 25, was prepared as follows:

16.5 g. (0.1 mol) of 3-bromo-3-methyl-2-butanone and 11.6 g. (0.12 mol) of potassium rhodanide were refluxed for 1–2 hours in 150 ml. of anhydrous acetone. After cooling, the separated potassium bromide was filtered under suction, back-washed with a small amount of acetone and evaporated to dryness in vacuo at 50° C. The residue was taken up in 200 ml. of ether and washed three times with 100 ml. of water. The ether phase was dried over sodium sulfate and evaporated to dryness in vacuo. The crude product was fractionated on a short Vigreux column to yield 3-methyl-3-thiocyanato-2-butanone, b.p. (0.04 mm), 52° C.

8.3 g. (0.12 mol) of hydroxylamine hydrochloride were dissolved in 50 ml. of water and treated with 10.1 g. (0.12 mol) of sodium hydrogen carbonate. This solution (pH 6–7) was added with stirring at room temperature to a solution of 14.3 g. (0.1 mol) of 3-methyl-3-thiocyanato-2-butanone in 100 ml. of ethanol. The temperature of the mixture rose rapidly to 37° C. The mixture was then stirred for 1 hour, 120 ml. of the solvent were then distilled off at 50° C. in vacuo. The residue was extracted three times with 100 ml. of ether each time. The organic phase was washed with a small amount of water, dried over sodium sulfate and concentrated until crystallization began. After cooling, the crystal sludge was treated with 10 ml. of hexane. The crystals were filtered off under suction, washed with ether/hexane (2:1) and dried to yield 2-oxo-4,5,5-trimethyl-3-thiazoline-oxime, m.p. 151°–153° C.

The starting materials used in Examples 6, 7, 9 and 13–24 were prepared in an analogous manner.

EXAMPLE 27

This example illustrates compositions containing a compound of formula I as the active ingredient.

| | g/liter |
|---|---|
| (a) Active Ingredient, a compound of formula I | 250 |
| N-methyl-2-pyrrolidone | 500 |
| Emulsifier mixture consisting of: | |
| calcium alkylarylsulfonate, | |
| alkylphenol ethoxylate, block polymerisate of propylene | |
| oxide and ethylene oxide | 50 |
| Calcium dodecylbenzenesulfonate | 25 |
| Solvent [mixture of mono-, di- and tri(lower alkyl)benzenes] | ad 1000 ml. |
| (b) Active Ingredient, a compound of formula I | 250 |
| N-methyl-2-pyrrolidone | ad 1000 ml. |
| (c) Active Ingredient, a compound of formula I | 50 g. |
| High-dispersible silicic acid | 5 g. |
| Sodium lauryl sulfate | 1 g. |
| Sodium lignosulfonate | 2 g. |
| Kaolin | 42 g. |
| | 100 g. |

I claim:

1. A pesticidal composition which comprises inert carrier material and, as the active ingredient, an amount which is effective as a pesticide of at least one compound of the formula

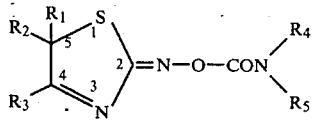

wherein $R_1$ and $R_3$ each are lower alkyl, lower alkenyl, cycloalkyl, aryl or halogen-substituted aryl; $R_2$ is lower alkyl; $R_4$ is lower alkyl or cycloalkyl; and $R_5$ is hydrogen, lower alkyl, lower alkylcarbonyl or halogen-substituted lower alkylcarbonyl and an acid addition salt thereof.

2. the pesticidal composition of claim 1 wherein the active ingredient is 2-oxo-4,4,5-trimethyl-3-thiazoline-O-(methylcarbamoyl)-oxime.

3. The pesticidal composition of claim 1 wherein the active ingredient is 2-oxo-4,5-dimethyl-5-ethyl-3-thiazoline-O-(methylcarbamoyl)-oxime.

4. The pesticidal composition of claim 1 wherein the active ingredient is 2-oxo-4,5-diethyl-5-methyl-3-thiazoline-O-(methylcarbamoyl)-oxime.

5. A method for the control of pests which comprises applying, to the site to be so treated, an amount of the pesticidal composition of claim 1 which is effective in the control of pests.

6. The method of claim 5 wherein the active ingredient of the pesticidal composition is 2-oxo-4,5,5-trimethyl-3-thiazoline-O-(methylcarbamoyl)-oxime.

7. The method of claim 5 wherein the active ingredient of the pesticidal composition is 2-oxo-4,5-dimethyl-5-ethyl-3-thiazoline-O-(methylcarbamoyl)-oxime.

8. The method of claim 5 wherein the active ingredient of the pesticidal composition is 2-oxo-4,5-diethyl-5-methyl-3-thiazoline-O-(methylcarbamoyl)-oxime.

9. A compound of the formula

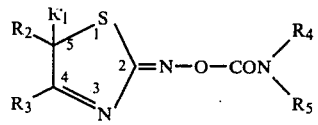

wherein $R_1$ and $R_3$ each are lower alkyl, lower alkenyl, cycloalkyl, aryl or halogen-substituted aryl; $R_2$ is lower alkyl; $R_4$ is lower alkyl or cycloalkyl; and $R_5$ is hydrogen, lower alkyl, lower alkylcarbonyl or halogen-substituted lower alkylcarbonyl and acid addition salts thereof.

10. A compound in accordance with claim 9 where $R_1$, $R_2$, $R_3$ and $R_4$ are each alkyl of from 1 to 3 carbons and $R_5$ is hydrogen.

11. A compound in accordance with claim 9, 2-oxo-4,5,5-trimethyl-3-thiazoline-O-(methylcarbamoyl)-oxime or an acid addition salt thereof.

12. A compound in accordance with claim 9, 2-oxo-4,5-dimethyl-5-ethyl-3-thiazoline-O-(methylcarbamoyl)-oxime or an acid addition salt thereof.

13. A compound in accordance with claim 9, 2-oxo-4,5-diethyl-5-methyl-3-thiazoline-O-(methylcarbamoyl)-oxime or an acid addition salt thereof.

14. A compound in accordance with claim 9, 2-oxo-4,5,5-trimethyl-3-thiazoline-O-(dimethylcarbamoyl)-oxime.

15. A compound in accordance with claim 9, 2-oxo-4-ethyl-5,5-dimethyl-3-thiazoline-O-(methylcarbamoyl)-oxime.

16. A compound in accordance with claim 9, 2-oxo-4-isopropyl-5,5-dimethyl-3-thiazoline-O-(methylcarbamoyl)-oxime.

17. A compound in accordance with claim 9, 2-oxo-4,5,5-trimethyl-3-thiazoline-O-(ethylcarbamoyl)-oxime.

18. A compound in accordance with claim 9, 2-oxo-4-phenyl-5,5-dimethyl-3-thiazoline-O-(methylcarbamoyl)-oxime.

19. A compound in accordance with claim 9, 2-oxo-4,5,5-trimethyl-3-thiazoline-O-(isopropylcarbamoyl)-oxime.

20. A compound in accordance with claim 9, 2-oxo-4,5,5-trimethyl-3-thiazoline-O-(cyclopropylcarbamoyl)-oxime.

21. A compound in accordance with claim 9, 2-oxo-4,5,5-trimethyl-3-thiazoline-O-(cyclobutylcarbamoyl)-oxime.

22. A compound in accordance with claim 9, 2-oxo-4-propyl-5,5-dimethyl-3-thiazoline-O-(methylcarbamoyl)-oxime.

23. A compound in accordance with claim 9, 2-oxo-4-cyclohexyl-5,5-dimethyl-3-thiazoline-O-(methylcarbamoyl)-oxime.

24. A compound in accordance with claim 9, 2-oxo-4,5-dimethyl-5-propyl-3-thiazoline-O-(methylcarbamoyl)-oxime.

25. A compound in accordance with claim 9, 2-oxo-4-propyl-5-ethyl-5-methyl-3-thiazoline-O-(methylcarbamoyl)-oxime.

26. A compound in accordance with claim 9, 2-oxo-4-butyl-5,5-dimethyl-3-thiazoline-O-(methylcarbamoyl)-oxime.

27. A compound in accordance with claim 9, 2-oxo-4,5-dimethyl-5-isobutyl-3-thiazoline-O-(methylcarbamoyl)-oxime.

28. A compound in accordance with claim 9, 2-oxo-4,5-dimethyl-5-pentyl-3-thiazoline-O-(methylcarbamoyl)-oxime.

29. A compound in accordance with claim 9, 2-oxo-4-(p-chlorophenyl)-5,5-dimethyl-3-thiazoline-O-(methylcarbamoyl)-oxime.

30. A compound in accordance with claim 9, 2-oxo-4,5-dimethyl-5-butyl-3-thiazoline-O-(methylcarbamoyl)-oxime.

31. A compound in accordance with claim 9, 2-oxo-4,5-dimethyl-5-(3-methyl-2-pentenyl)-3-thiazoline-O-(methylcarbamoyl)-oxime.

32. A compound in accordance with claim 9, 2-oxo-4,5,5-trimethyl-3-thiazoline-O-[methyl(acetyl)carbamoyl]-oxime.

33. A compound in accordance with claim 9, 2-oxo-4,5-dimethyl-5-ethyl-3-thiazoline-O-[methyl(acetyl)carbamoyl]-oxime.

* * * * *